(12) United States Patent
Stabler et al.

(10) Patent No.: US 6,836,681 B2
(45) Date of Patent: Dec. 28, 2004

(54) METHOD OF REDUCING STRESS

(76) Inventors: Jon R. Stabler, 2 Blue Heron, Boeme, TX (US) 78005; Deborah G. Stabler, 2 Blue Heron, Boeme, TX (US) 78005

( * ) Notice: Subject to any disclaimer, the term of this patent is extended or adjusted under 35 U.S.C. 154(b) by 277 days.

(21) Appl. No.: 10/077,091

(22) Filed: Feb. 15, 2002

(65) Prior Publication Data

US 2002/0111555 A1 Aug. 15, 2002

Related U.S. Application Data

(60) Provisional application No. 60/269,782, filed on Feb. 15, 2001.

(51) Int. Cl.[7] .............................................. A61B 5/04
(52) U.S. Cl. ........................................ 600/515; 600/26
(58) Field of Search ................................. 600/9, 26–28, 600/509, 515, 519, 523; 128/905; 607/9, 26–28

(56) References Cited

U.S. PATENT DOCUMENTS

| | | | | | |
|---|---|---|---|---|---|
| 4,355,644 A | * | 10/1982 | Saito | ........................... | 600/502 |
| 4,683,891 A | * | 8/1987 | Cornellier et al. | ........... | 600/301 |
| 4,819,656 A | * | 4/1989 | Spector | ....................... | 600/549 |
| 5,163,439 A | * | 11/1992 | Dardik | ........................ | 600/508 |
| 5,253,168 A | * | 10/1993 | Berg | ............................ | 600/301 |
| 6,212,427 B1 | * | 4/2001 | Hoover | ........................ | 600/515 |
| 6,305,943 B1 | * | 10/2001 | Pougatchev et al. | ......... | 434/262 |
| 6,306,077 B1 | * | 10/2001 | Prabhu et al. | ................. | 600/26 |
| 6,554,763 B1 | * | 4/2003 | Amano et al. | ................ | 600/26 |

* cited by examiner

*Primary Examiner*—Mark Bockelman
(74) *Attorney, Agent, or Firm*—Kolisch Hartwell, P.C.

(57) ABSTRACT

A method of enabling a person to reduce tension as a way of improving the possibility that the person will reach a desired level of performance during a tension-causing event includes the steps of selecting a monitor capable of measuring the heart rate of a person and including a display constructed to show heart-rate variability (HRV), and connecting a person to the monitor. The method also includes allowing the person to view the display of their own HRV while connected to the monitor, communicating to the person a desired range of HRV and an undesired range of HRV, and teaching the person how to breath to reach the desired range of HRV and to verify that the person reached the desired range of HRV by viewing the display. In addition, the method includes directing the person to think of a tension-causing event; and repeating the teaching step until the person reaches the desired range of HRV while thinking of the tension-causing event. The method could also include the steps of selecting a monitor that is portable, directing the person to perform a tension-causing event, and repeating the teaching step until the person reaches the desired range of HRV while performing the tension-causing event.

4 Claims, 2 Drawing Sheets

METHOD OF REDUCING STRESS

CROSS-REFERENCE TO RELATED APPLICATIONS

This application claims priority to U.S. Provisional Patent Application Ser. No. 60/269,782, filed Feb. 15, 2001 and entitled "Method of reducing stress", which is hereby incorporated by reference.

The present invention is usable by a person to allow them to increase focus and reduce tension associated with any event in the person's life, such as a sporting event (if the person is an athlete) or testing event (if the person is a student). For purposes of the description of the method of the invention below, the method will be described in the context of a person who plays golf. However, it should be understood that the method of the invention has much broader application to other sporting events as well as any other tension-causing events including academic testing.

The method or sequence of steps involved in the present invention enables a person to learn how to clear their minds and reduce their level of tension to desirable levels for optimum performance in their sport. We have found that most people have little ability to control their level of tension or their thoughts. In fact most people have no awareness of their level of tension or the impact of their thoughts on their physiology.

Our thoughts trigger responses in our physiology. The effects of our thoughts on our bodies can be measured in many ways. Some of the aspects of our physiology that change are: brain waves, muscle tension, heart rate, skin temperature, perspiration, heart rate variability, muscle contractions, releases of chemicals such as adrenaline, epinephrine, norepinephrine, cortisol, etc. The methods of measurement can be simple, immediate and non-invasive or more complex, invasive and delayed. Through our research and testing, we have determined that heart rate variability is one of the most sensitive and easily measured of the physiological functions and well-suited to the widest possible applications.

The autonomic nervous system (ANS) is the portion of the nervous system that controls the body's visceral functions, including the action of the heart, the movements of the gastrointestinal tract and the secretion by different glands, among many other vital activities. It is well known that mental and emotional states directly affect the ANS. Many research studies have examined the influence of emotions on the ANS utilizing the analysis of heart rate variability, which serves as a dynamic window into autonomic function and balance. Heart rate variability (HRV), derived from the electrocardiogram (ECG), is a measurement of the beat-to-beat changes in heart rate. The normal variability in heart rate is due to the synergistic action of the two branches of the ANS, which act in balance through neural, mechanical, humoral and other physiological mechanisms to maintain cardiovascular parameters in a healthy individual, thus, the heart rate estimated at any given time represents the net effect of the parasympathetic (vagus) nerves, which slow heart rate, and the sympathetic nerves, which accelerate it. These changes are influenced by emotions, thoughts and physical exercise. Our changing heart rhythms affect not only the heart but also our brain's ability to process information, including decision-making, problem-solving and creativity. They also directly affect how we feel.

We know from other studies that when we are stressed the parasympathetic nervous system shuts down allowing the sympathetic nervous system to accelerate the heart. This used to be a very valuable response to enable us to survive dangerous situations. It is commonly referred to as "Fight or Flight" responses. Unfortunately, many of us maintain an unhealthy level of stress much of the time. Individually we do not recognize our levels of stress nor it's impact on our health, happiness, productivity or effectiveness.

The mathematical transformation (Fast Fourier Transform) of the HRV data into power spectral density is used to discriminate and quantify sympathetic and parasympathetic activity and total autonomic nervous system activity. The power spectrum is divided into 3 frequency ranges. The very low frequency range (VLF) (0.0033 to 0.04 Hz), is an index of sympathetic activity, while power in the high frequency range (HF) (0.15 to 0.4 Hz), is primarily due to parasympathetic activity. The graph shown in FIG. 1 is from an HRV-data measuring device that shows the power levels and the typical form when the two systems are in balance, that is the subject has achieved a level of passive awareness where the mind is peaceful and quiet.

Showing a peak form in the 0.05 to 0.15 range is only possible when the subject is peaceful and the sympathetic and parasympathetic systems are quiet and in balance. The horizontal axis shows the Hz range from 0.00 to 0.40. The vertical axis indicates the activity or energy level. This vertical axis is adjustable from 0.0 to 5.0 depending on the subject. We have found younger subjects have greater amplitude on the vertical scale.

In summary, and as described further below in connection with one application, the method of the invention enables a person to reduce tension as a way of improving the possibility that the person will reach a desired level of performance during a tension-causing event includes the steps of selecting a monitor capable of measuring the heart rate of a person and including a display constructed to show heart-rate variability (HRV), and connecting a person to the monitor. The method also includes allowing the person to view the display of their own HRV while connected to the monitor, communicating to the person a desired range of HRV and an undesired range of HRV, and teaching the person how to breath to reach the desired range of HRV and to verify that the person reached the desired range of HRV by viewing the display. In addition, the method includes directing the person to think of a tension-causing event; and repeating the teaching step until the person reaches the desired range of HRV while thinking of the tension-causing event. The method could also include the steps of selecting a monitor that is portable, directing the person to perform a tension-causing event, and repeating the teaching step until the person reaches the desired range of HRV while performing the tension-causing event.

STEPS OF METHOD OF THE INVENTION

1. Currently the client is present in person. The objective of achieving a state of passive awareness is presented to the client in terms that compare it to the Zone or the Champion range of tension. Explanation is made of the "Fight or Flight" responses and how those reactions are detrimental to performance in golf competition. As the client climbs the tension scale, their golf abilities decline, i.e.; their focus widens, their mind gets busier, their ability to visualize is impaired, their ability to make good decisions declines, they lose intuitive ability, they lose fine motor control of small muscles, their tempo quickens, their big muscles tighten, etc. The client is advised that the only reason they climb the tension scale is because of their thoughts.

2. With the client's permission, electrodes are attached to the skin of their torso. A strap with tension sensing capability is wrapped around their abdominal area. In addition the sensor belt of a heart rate monitor, or Advanced Zone Trainer (AZT), with heart rate capability is belted around their chest with the electrode sensor near the heart. The client is typically seated in front of a computer monitor to begin.

Figure 1:
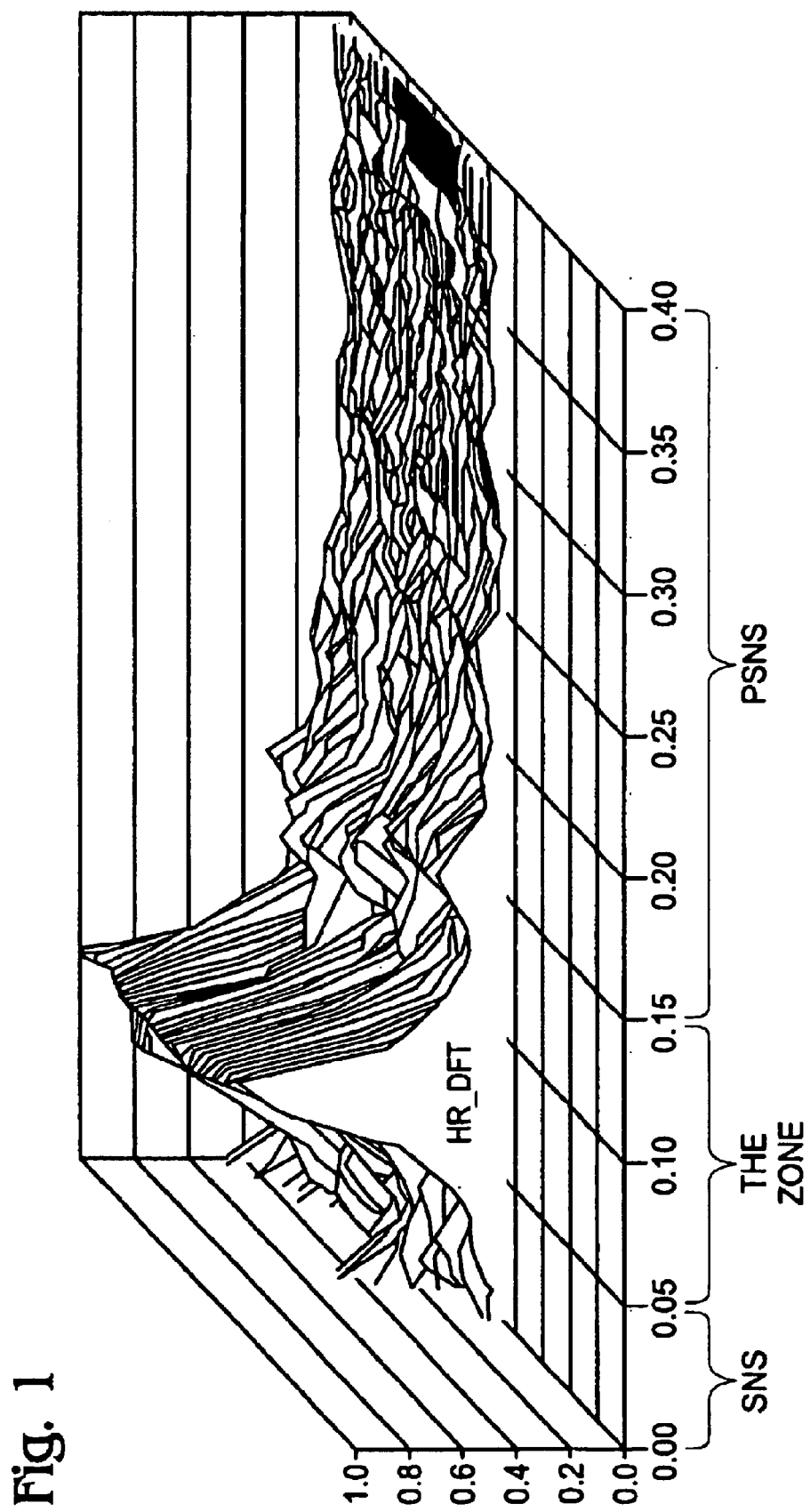
FIG. 1 illustrates graphically how a person using the method of the invention would reduce tension by showing HRV data for such a person, and identifying SNS (Sympathetic Nervous System), and PSNS (Parasympathetic Nervous System).
Figure 2:
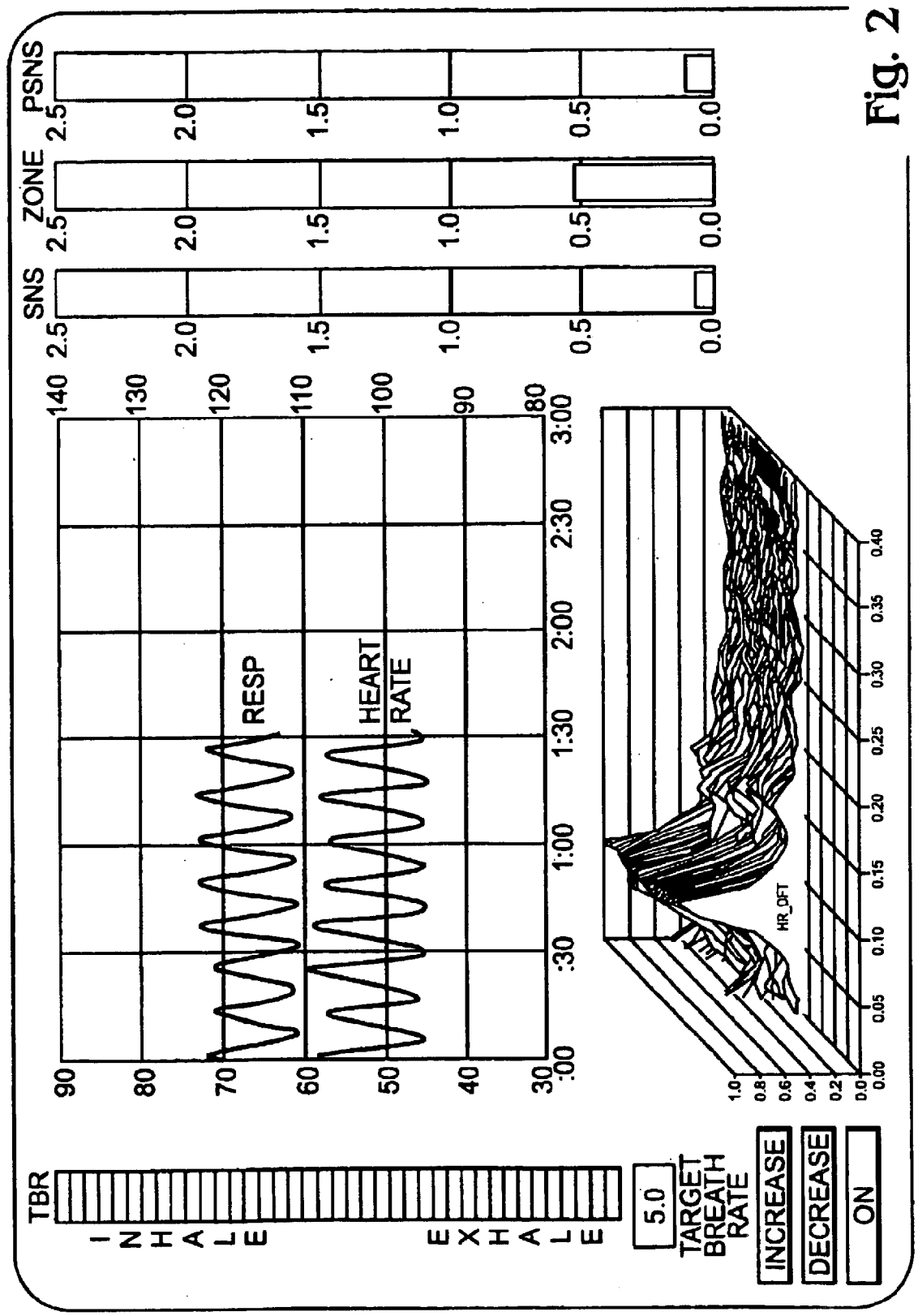
FIG. 2 illustrates a typical computer display associated with the vital signs of a client that are monitored while practicing the method of the invention.

3. The first set of electrodes is connected directly to the computer. The tension sensor is also connected to the computer. Data from these electrodes and the tension sensor is routed to our proprietary software for analysis and incorporation into the video display (see FIG. 2).

4. The AZT output is sent by radio waves to a watch-like wrist receiver within 3 feet of the client for analysis and display.

5. The computer software program is activated and the client information entered. Adjustments are made to display the data on the computer screen so it is visible on the graphic representations. For example: with young clients the amplitude of their heart rate may range off the graph. Adjustments are made so that the full range of their changing heart rate fits on the graphic display. The AZT is also activated and adjusted appropriately for the client.

6. The client is then asked to watch a guide that is cycling at a controlled rate. We typically start at 6 cycles per minute. They are to breath with this guide, that is 6 breaths per minute. This is much slower than the typical 14–22 or more breaths per minute they typically do. In addition they are instructed in the manner of breathing, i.e.: to breath abdominally using their diaphragm, as they inhale their abdomen should push out, as they inhale the abdomen should be pulled in, pushing the air out of the lungs. They are to focus their attention on the guide and their breathing attempting to inhale and exhale in similar manner, a controlled, continuous flow of air. The objective is not to completely exhaust nor fill their lungs. The rate of the breathing guide is adjusted to their comfortable rate which may be faster or slower than the initial rate. The change of length of the tension strap around the abdomen caused by breathing in this manner is displayed on the same graph with heart rate and shows the method and amplitude of their breathing.

7. Some amount of time is allowed to pass in this breathing mode. If the client is focused on the breathing guide and their own efforts to breath then we may observe that the SNS level of activity is decreasing and the energy in The Zone portion of the spectral display is rising or peaking. They are achieving the Zone state or balance of SNS and PSNS. If so, they are advised that they are in The Zone and to notice how it feels and how quiet their mind is. We should also see the heart rate following the breathing, i.e., as the client inhales the heart rate rises, as the client exhales the heart rate falls. This effect is called respiratory sinus arrhythmia (RSA).

8. Typically they will need more direction to quiet their thoughts. We know this because we will see more energy in the SNS portion of the spectral display and the heart rate graph will be erratic relative to the breathing graph. If the SNS area shows higher energy, this indicates that their minds are busy and they may be working too hard at trying to breath. We inquire what they were thinking about and make them more aware of their thoughts. We direct them to be in the moment, to push away any thoughts that come in or external distractions that are gaining their attention. Often we ask them where they are the most relaxed and to imagine being there. This coaching with valid real-time feedback for us and the client is extremely effective. We know when they are doing it right. They know what they are doing to quiet their mind and SNS. When the computer program indicates they are in The Zone, we observe the Heart Rate Variability readout on the wrist device of the heart rate monitor. We do this to correlate the numbers on the wrist device with The Zone. Later the readout on the wrist device is used on the golf course. Every client is different, so we must find each individual's range for The Zone.

9. Once they have experienced The Zone, we increase the degree of difficulty. We ask them to close their eyes and continue breathing and return to The Zone. We may coach them on their breathing to give them more confidence in their rate of breathing. We also coach them to achieve The Zone as above. When SNS increases, we ask what they were thinking. When they achieve The Zone, we ask them to recognize they are there and notice how it feels and what they are doing mentally and physically to stay there. After they reach The Zone with eyes closed we move to a more difficult step.

10. The next step is to have them stand up facing the computer, eyes open and reach The Zone.

11. Then standing with eyes closed and reach The Zone.

12. Then standing with eyes open looking out the window. There will be distractions in their vision. We work with them to get to The Zone no matter what is passing in front of them.

13. After they have achieved The Zone in each of these ways, seated again and eyes closed, we ask them to remember a golf shot that they had problems with. They should visualize it very vividly, remembering the weather, the situation, the variables of the shot. Then we step them through a mental pre-shot routine. This is the mental pre-shot routine we developed and teach to all of our clients. If-they are doing a good job of visualizing, we see an uptick in SNS activity and a decrease in HRV and respiratory sinus arrhythmia. They are to do all three steps of the Mental Pre-Shot Routine and then hit the shot when they are ready in their imaginations. Most of the time, they report hitting a good shot or a better shot than they did before. They also report feeling better tempo and more relaxed over the shot. They are then directed to return to The Zone.

14. Sometimes we see a large increase in SNS activity and the client struggles with the shot in their imagination. When this occurs, we question for the source of the anxiety reaction they are feeling. Most of the time it is due to a lack of confidence in the club or type of shot they are attempting. Sometimes it is due to a conditioned response they have developed from similar situations where they have performed poorly (sometimes referred to as the Yips). If it is a lack of confidence we encourage them to make another choice they have more confidence in. Generally, the change of club or target will enable them to go forward with lowered SNS activity and experience a good imaginary shot.

15. Where we are working with a conditioned response, this methodology and instant feedback is very effective to uncondition their conditioning. In addition to the feedback of SNS activity and reduced RSA, we must get them to change their goals and attitude about this particular part of their game. They must agree to make unconditioning more important than score or outcome of the shot. Then they must look forward to each time they have to play this shot as an opportunity to change their conditioning. From the moment they know that the next shot is the feared kind, they are to work on breathing and reaching RSA and take their mind away from the situation. If they have an AZT, they are to observe the measurement of HRV and attempt to increase it. Then when it is time to play the shot, they are to do the very best mental pre-shot routine they can, emphasizing the process and not the outcome. In a very short period of time conditioned responses that they have had for years can be unconditioned.

16. The next step is to do an imaginary shot standing with eyes closed.

17. From this point we disconnect from the computer and still wearing the AZT, go to the range, the putting green and the golf course.

18. On the practice range, the client is allowed to stretch and hit balls until they feel they are warmed-up. We then observe the HRV numbers on the AZT display. If HRV has decreased, the client is asked to breath and attempt to reach The Zone. This can take some time depending on the client's thoughts about the situation. If struggling, we explore for the thoughts that are making this difficult. Once they have improved their HRV, then we instruct them to hit a golf shot using a good mental pre-shot routine. We pick the target. They choose the club and shape of shot. The HRV value is observed. If it has deteriorated, they are asked to pause and get back into The Zone. The client then plays the shot. We immediately observe the HRV value after the shot. We now have measurements of HRV before and after the shot. There are two classic scenarios. In scenario A, the client has good HRV numbers before the shot and not after. In scenario B, the client has poor HRV values before the shot and better HRV values after the shot. We interpret scenario A to mean the client is comfortable before the shot and immediately begins analyzing the results after the shot. In scenario B the client is anxious or uncomfortable with the shot before hand and then relaxes after the shot because it is over and the anxiety abates. Our goal for the client is to achieve good HRV values before and after the shot. This process makes them much more aware of their thought process and the effects of the thought process on their performance. It also makes them aware of their level of tension.

19. From the practice range we proceed to the practice putting green. There we go through the same steps as on the range. The connection between mental processes and level of tension and the effect on performance is more obvious here. The client must get more relaxed or have lower tension here than on the practice range to putt and chip well.

20. The next step is to go onto the golf course. Typically, the client experiences lower HRV values because they feel more pressure on the course. The outcomes of their shots count. Again, we push them to improve their HRV values. We explore the thoughts that are hurting the HRV values. We get them to breath, quiet their minds and reach The Zone which improves their performance. This completes a full initial session of this GolfPsych Method.

21. The client is then instructed to work on their breathing technique and mind clearing daily. They may purchase an AZT to work with at home. We set mental goals of achieving specific HRV values on the course and raising their maximum HRV values at home in their off-course practice.

22. At subsequent sessions the client may be hooked up to the computer and AZT again and go through this same process for practice and improvement.

The ability to control your level of tension at a level that is beneficial to your performance is valuable for most sports and to performance in other areas of life. This process of learning to breath and clear your mind and achieving a lower level of tension can be applied everywhere and anytime. It can help children with test anxiety to test better. It can help people in business to prepare for a meeting or presentation. It can help employees perform better and more productively. By lowering stress, it can have major health benefits and relationship benefits.

I claim:

1. A method of enabling a person to reduce tension as a way of improving the possibility that the person will reach a desired level of performance during a tension-causing event, comprising:

selecting a monitor capable of measuring the heart rate of a person and including a display constructed to show heart-rate variability (HRV);

connecting a person to the monitor;

allowing the person to view the display of their own HRV while connected to the monitor;

communicating to the person a desired range of HRV and an undesired range of HRV;

teaching the person how to breath to reach the desired range of HRV and to verify that the person reached the desired range of HRV by viewing the display;

directing the person to think of a tension-causing event; and repeating the teaching step until the person reaches the desired range of HRV while thinking of the tension-causing event.

2. The method of claim 1, further including the steps of:

selecting a monitor that is portable;

directing the person to perform a tension-causing event;

repeating the teaching step until the person reaches the desired range of HRV while performing the tension-causing event.

3. The method of claim 1, wherein the teaching step includes the step of providing the person with a guide for breathing at a desired, relatively low rate.

4. The method of claim 2, wherein the teaching step includes the step of providing the person with a guide for breathing at a desired, relatively low rate.

* * * * *